United States Patent
Muto et al.

(10) Patent No.: US 8,455,824 B2
(45) Date of Patent: Jun. 4, 2013

(54) CHARGED PARTICLE BEAM APPARATUS, AND SAMPLE PROCESSING AND OBSERVATION METHOD

(75) Inventors: Hiroyuki Muto, Hitachinaka (JP); Tsuyoshi Ohnishi, Hitachinaka (JP); Isamu Sekihara, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/601,893

(22) Filed: Aug. 31, 2012

(65) Prior Publication Data

US 2012/0326028 A1 Dec. 27, 2012

Related U.S. Application Data

(63) Continuation of application No. 12/175,940, filed on Jul. 18, 2008, now abandoned.

(30) Foreign Application Priority Data

Jul. 20, 2007 (JP) ................................. 2007-188986

(51) Int. Cl.
*H01J 45/00* (2006.01)
*H01J 37/04* (2006.01)
*G01N 23/225* (2006.01)

(52) U.S. Cl.
USPC .................... 250/310; 250/492.21; 250/492.3

(58) Field of Classification Search
USPC ................... 250/306, 307, 309–311, 440.11, 250/441.11, 442.11, 492.1, 492.21, 492.3
See application file for complete search history.

(56) References Cited

U.S. PATENT DOCUMENTS

| | | | |
|---|---|---|---|
| 5,525,806 A | 6/1996 | Iwasaki et al. | |
| 5,844,416 A * | 12/1998 | Campbell et al. | ........ 324/754.21 |
| 6,664,552 B2 | 12/2003 | Shichi et al. | |
| 6,794,663 B2 | 9/2004 | Shichi et al. | |
| 6,822,245 B2 | 11/2004 | Muto et al. | |

(Continued)

FOREIGN PATENT DOCUMENTS

| | | |
|---|---|---|
| JP | 06-231719 A | 8/1994 |
| JP | 06-231720 A | 8/1994 |

(Continued)

OTHER PUBLICATIONS

Kato et al., "Introduction of an FIB/SEM Dual Beam Device Utilizing a Three-dimensional 'Slice & View' Function", The TRC News, No. 84, pp. 40-43, Jul. 2003.

(Continued)

*Primary Examiner* — Bernard E Souw
(74) *Attorney, Agent, or Firm* — McDermott Will & Emery LLP

(57) ABSTRACT

An object of the present invention relates to realizing the processing of a sample by charged particle beams and the monitoring of the processed cross-section with a high throughput. It is possible to process an accurate sample without an intended region lost even when the location and the size of the intended region are unknown by: observing a cross-sectional structure being processed by FIBs by using a secondary particle image generated from a sample by the ion beams shaving a cross section; forming at least two cross sections; and processing the sample while the processing and the monitoring of a processed cross section are carried out.

2 Claims, 15 Drawing Sheets

U.S. PATENT DOCUMENTS

| | | |
|---|---|---|
| 6,979,822 B1 | 12/2005 | Stewart et al. |
| 7,071,713 B2 * | 7/2006 | Furukawa et al. ....... 324/750.19 |
| 7,084,399 B2 | 8/2006 | Muto et al. |
| 7,235,798 B2 | 6/2007 | Ishitani et al. |
| 7,268,356 B2 | 9/2007 | Shichi et al. |
| 7,592,606 B2 | 9/2009 | Ishiguro et al. |
| 7,615,765 B2 | 11/2009 | Katagiri et al. |
| 2002/0079463 A1 | 6/2002 | Shichi et al. |
| 2003/0127595 A1 | 7/2003 | Nakamura et al. |
| 2004/0089821 A1 | 5/2004 | Shichi et al. |
| 2005/0006600 A1 | 1/2005 | Shichi et al. |
| 2005/0045821 A1 | 3/2005 | Noji et al. |
| 2005/0279952 A1 | 12/2005 | Ishitani et al. |
| 2006/0169900 A1 | 8/2006 | Noji et al. |
| 2007/0102650 A1 | 5/2007 | Katagiri et al. |
| 2008/0018460 A1 | 1/2008 | Ishiguro et al. |
| 2008/0067443 A1 * | 3/2008 | Todoroki et al. ......... 250/492.21 |
| 2008/0191151 A1 | 8/2008 | Shichi et al. |
| 2008/0283746 A1 * | 11/2008 | Ohnishi ........................ 250/307 |
| 2009/0020698 A1 * | 1/2009 | Muto et al. .................... 250/310 |
| 2009/0134327 A1 * | 5/2009 | Ikku et al. ..................... 250/307 |
| 2012/0199758 A1 * | 8/2012 | Kawanami et al. ........... 250/397 |

FOREIGN PATENT DOCUMENTS

| | | |
|---|---|---|
| JP | 08-115699 A | 5/1996 |
| JP | 10-162766 A | 6/1998 |
| JP | 2001-229869 A | 8/2001 |
| JP | 2004-228076 A | 8/2004 |
| JP | 2006-127850 A | 5/2006 |
| JP | 2007-018934 A | 1/2007 |
| JP | 2007-193977 A | 8/2007 |
| WO | WO-2006/050613 A1 | 5/2006 |

OTHER PUBLICATIONS

Japanese Notice of Rejection, w/ English translation thereof, issued in Japanese Patent Application No. JP 2007-188986 dated Feb. 9, 2010.

Japanese Notice of Rejection, w/ English translation thereof, issued in Japanese Patent Application No. JP 2007-188986 dated Nov. 10, 2009.

* cited by examiner

CHARGED PARTICLE BEAM APPARATUS, AND SAMPLE PROCESSING AND OBSERVATION METHOD

CLAIM OF PRIORITY

The present application is a continuation application of U.S. application Ser. No. 12/175,940, filed on Jul. 18, 2008 now abandoned, which claims priority from Japanese patent application serial No. 2007-188986 filed on Jul. 20, 2007, the content of which is hereby incorporated by reference into this application.

BACKGROUND OF THE INVENTION

1. Field of The Invention

The present invention relates to a technology of processing and observing a sample by charged particle beams, and for example to a charged particle beam apparatus to produce a processed surface on a fine sample extracted from a substrate of a semiconductor device by applying microprocessing to a specific portion by FIBs (Focused Ion Beam) and observe the processed surface with a scanning transmission electron microscope (STEM), a transmission electron microscope (TEM), a scanning electron microscope (SEM), or the like.

2. Description of the Related Art

A technology on the combination of an FIB apparatus and an STEM apparatus is disclosed in Japanese Patent Laid-Open No. 2004-228076. It shows that an STEM observation sample produced by FIB processing is placed at the intersection of an ion beam axis and an electron beam axis and can be subjected to additional FIB processing and STEM observation. The ion beam axis and the electron beam axis intersect at acute angles (about 45 degrees in the case shown FIG. 5) and the STEM sample is rotated around a rotation shaft perpendicular to both the axes during the time between the additional FIB processing and the STEM observation.

Further, Japanese Patent Laid-open No. 2006-127850 describes a technology of realizing: the omission and minimization of the sample rotation or the like during the time between the FIB processing and the STEM observation; and the simplification in the operation of optimizing a sample thickness with an STEM image monitor during processing. According to the technology, an ion beam system, an electron beam system, and a transmitted and scattered beam detection device are disposed around a sample, the illumination axis of the FIB system and the illumination axis of the electron beam system for STEM observation are arranged so as to form nearly right angles to each other, and the sample is placed at the intersection. By so doing, it is possible to carry out both the FIB processing and the STEM observation without the sample displaced.

THE TRC NEWS No. 84, July, 2003 (Kato and Otsuka, Toray Research Center, Inc.) describes a means of three-dimensional structural analysis by FIB processing and SEM observation. Both the illumination axes of the FIB system and the electron beam system intersect with each other at acute angles and it is possible to display an image in the same region with the scanned images of both the beams, namely with the scanning ion microscopic image (the SIM image) and the SEM image. As it is anticipated from the electron beam system, by processing across section by FIBs, it is possible to observe the processed cross section with an SEM without the sample inclined. By repeating the FIB processing and the SEM observation, it is possible to integrate continuous segmented images in the direction of the depth from the processed surface.

The FIB processing and the STEM observation have heretofore been carried out with separate apparatuses in many cases. A thin film sample for an STEM processed with an FIB apparatus had to be once extracted from the FIB apparatus, and thereafter observed with an STEM apparatus. Thin film processing wherein an observed portion was identified by repeating the STEM observation and the additional FIB processing could not meet users' needs sufficiently from the viewpoint of throughput. To cope with the problem, an apparatus integrating FIB processing and STEM observation is announced and the improvement of throughput is attempted.

However, in such a case as to process a sample the exact defective portion and the defect size of which are not known into a thin film while an intended defective portion is retained, drastic improvement in throughput has not been attained yet because of the reasons: (1) a thin film sample larger than an ordinary sample is produced; (2) the repetition of FIB processing and SEM or STEM observation by cross section monitoring is carried out more frequently than usual and thin film processing is carried out while the observation portion is judged; (3) the region of processing itself expands; and others.

The fact that a cross section cannot be observed with an SEM or an STEM during FIB processing is one of the factors that cause throughput to be prevented from improving. Further, in the case of a sample having plural cross sections such as a thin film sample, when the plural cross sections are observed with an SEM or an STEM, displacement operation such as rotation and inclination of the sample or a sample stage is necessary in order to irradiate the cross section to be observed with electron beams. Furthermore, once a sample is displaced, visual field readjustment and focus readjustment are required. From those factors, even an apparatus integrating FIB processing and STEM observation can hardly secure a sufficient throughput.

In the case of three-dimensional structural analysis by FIB processing and SEM observation too, there are similar problems since the FIB processing and the SEM observation are repeated alternately. When the three-dimensional structural analysis is applied to a large region, visual field deviation and focus deviation appear in an SEM observed cross-sectional image as the FIB processing advances, hence it is necessary to adjust the visual field and the focus of the SEM frequently, and such operation is a factor causing the throughput to deteriorate.

Further in recent years, in order to realize a microstructure having high electrical characteristics, a material called a Low-K material that is very susceptible to electron beam irradiation has come to be used much and the cases of destroying or deforming a sample by electron beam irradiation during SEM observation and the like have come to happen frequently. The Low-K material is a low permittivity materials made of, for example, organic polymer or SiOC etc. As measures against the cases, means such as (1) to mitigate damage by cooling a sample, (2) to extremely lower the acceleration voltage of electron beams and reduce irradiation energy, and others have been taken.

However, the means (1) requires time for cooling and exchanging samples and the throughput of processing lowers enormously. Further, the damage caused by electron beam irradiation appears locally and the observed portion deforms even though the sample stage is cooled unless a cooling path is sufficiently secured. A drawback of the means (2) is that the image resolution of an SEM lowers by lowering the acceleration voltage of electron beams and the microstructure is hardly recognized.

SUMMARY OF THE INVENTION

An object of the present invention is to process a sample by charged particle beams and monitor the processed cross section with a high throughput.

The present invention relates to observing a cross-sectional structure during FIB processing as a secondary particle image generated from a sample by using ion beams shaving the cross section.

The present invention makes it possible to observe a cross section by ion beams used for processing.

DETAILED DESCRIPTION OF THE PREFERRED EMBODIMENTS

Figure 1A:
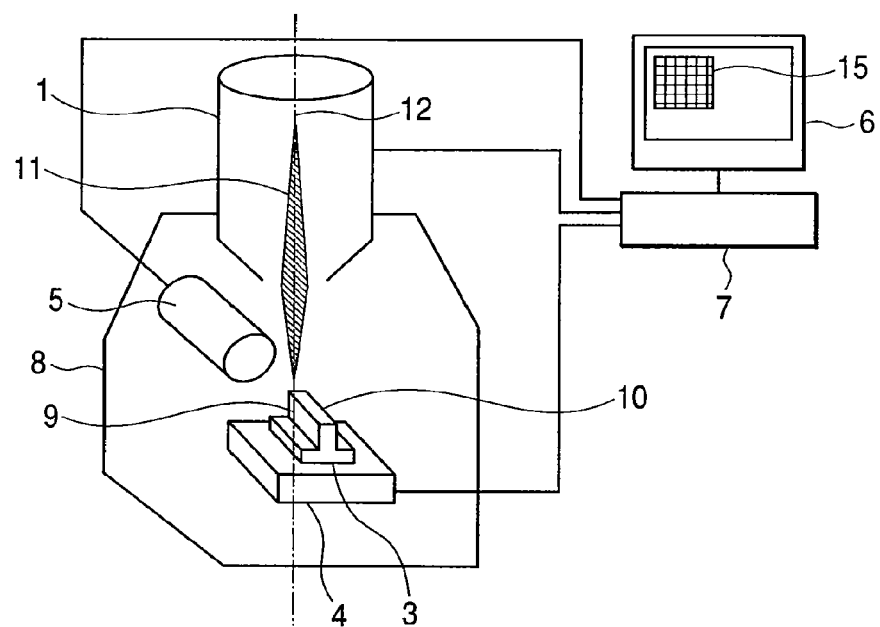
FIGS. 1A and 1B are general configuration diagrams of a charged particle beam apparatus having an ion beam system.

The present inventors have earnestly studied and obtained the following knowledge.

In order to produce an accurate sample while an intended defective region is retained even though the location and size of the defect in the sample is unknown, it is necessary to produce at least two cross sections and advance the processing of the sample while the processing and the monitoring of the processed cross sections are carried out. A high throughput in processing and monitoring of a processed cross section may be obtained by: observing a cross-sectional structure during FIB processing as a secondary particle image generated from a sample by using ion beams shaving the cross section; and thereby making it possible to carry out both the processing and the observation at the same time. By so doing, it is possible to obtain a high throughput also in the process of repeating the processing and the monitoring of the processed cross sections and analyzing the structure of the sample.

At the final stage of shaving a cross section, a fabrication area forms a shape of a strip and usually an observed image also has a strip shape. The end point of the processing has heretofore been judged by the average brightness of a whole observed image. Consequently, although the process of advancing cross-sectional processing from the surface toward the sample substrate has roughly been obtained, the structure of the cross section has hardly been obtained. To cope with the problem, the combined use of an SEM has been studied. In the present invention, the observation is arranged so as to be displayed expansively in the direction of the short side of the strip shape and the cross-sectional structure is arranged so as to be obtained only by FIBs during processing.

In general, a processed cross section is formed by FIB processing so as to incline at an angle of several degrees to the incident angle of ion beams in consideration of the relationship between a local angle of the ion beams incoming to a sample and a sputtering efficiency (J. Vac. Sci. Technol. B9(5), September/October 1991, pp 2636). In the present invention, a cross-sectional structure can be displayed by: using the physical phenomenon; setting a strip-shaped fabrication area at an inclined portion; and displaying the processing monitor expansively in the short side direction. Although the image resolution deteriorates worse than the beam diameter since the beams are applied from a direction oblique to, nearly parallel with, the cross section, it is possible to display an image that is sufficient in obtaining a cross-sectional structure such as the existence of a wiring structure. The cross-sectional structure is observed by using the function and, when an intended cross section is not attained yet, the fabrication area shifts in the direction of the cross section and the processing and the judgment of the cross-sectional structure are repeated. By so doing, it is possible to attain an intended cross section without the combined use of an SEM.

A region requiring high resolution observation with an SEM, an STEM, or a TEM is only a part of a sample and hence the other region not requiring high resolution observation is subjected to the aforementioned FIB processing observation and, when another region requiring high resolution observation appears, the FIB processing observation is switched to SEM, STEM, or TEM observation. By so doing, it is possible to reduce stage shift and switching operation between FIB processing and SEM, STEM, or TEM observation.

Even in the case of using three-dimensional structural analysis by FIB processing and SEM observation and a material that is very susceptible to electron beam irradiation, a region requiring high resolution observation with an SEM, an STEM, or a TEM is only a part of a sample. Consequently, the other region not requiring high resolution observation is subjected to the aforementioned FIB processing observation and, when another region requiring high resolution observation appears, the FIB processing observation is switched to SEM, STEM, or TEM observation. By so doing, it is possible to: reduce the visual field readjustment and the focus readjustment of an SEM observed cross-sectional image that is required as the FIB processing advances; and also reduce the amount of electron beams applied to a material that is very susceptible to electron beam irradiation.

In the present invention, it is possible to produce an accurate sample with a high throughput while an intended region is retained even though the exact defective portion of the sample is not known in the process for producing the sample such as a thin film while processing and monitoring of a processed cross section are repeated. Further, in the process for repeating processing and monitoring of a processed cross section and applying three-dimensional structural analysis to a sample too, the throughput of the analysis can be improved. Moreover, it is possible to observe a cross section infinitely close to a true appearance even with a material that is very susceptible to electron beam irradiation.

Since the processing and observation of a cross section can be simultaneously carried out by ion beams used for the processing, it is possible to reduce: stage transfer for monitoring the cross section during processing; SEM visual field adjustment; and SEM focus adjustment. Further, since the processing and observation are carried out by ion beams incoming perpendicularly to the sample surface, the location where a cross section is formed is not restricted. Consequently, however an intended region is placed, vertically, transversely, or obliquely, as long as at least two cross sections are formed and processing and monitoring are repeated, it is possible to retain the intended region without fail. Also when plural processed cross sections are monitored, it is not necessary to move a stage in order to monitor a cross section except the case of high-resolution observation using an SEM, an STEM, or a TEM. In addition, it is not necessary to readjust the focus of ion beams since the position of a sample is not changed. In the present invention, unnecessary stage transfer, accompanying beam adjustment, SEM, STEM, or TEM observation for cross section monitoring can be avoided and hence it is possible to carry out with a high throughput the process accompanying continuous or intermittent processing and the monitoring of a processed cross section, for example aforementioned production of a thin film sample and three-dimensional structural analysis. Further, information on a cross section that has not been obtained during FIB processing can be obtained and the information on a cross section can be obtained not only as discrete data but also as continuous motion picture data.

Further, since an intended cross section can be formed without the combined use of an SEM, it is possible to carry out FIB cross section processing and thin film processing while damage and deformation in a cross section of a sample susceptible to electron beam irradiation are inhibited. A cross section to which the FIB processing is applied in a vacuum is clean and has no impurities such as an adsorption gas and hence, by installing an FIB, an SEM, an STEM, or the like in an identical vacuum chamber, it is possible to observe at a high resolution an unlimitedly clean surface having: extremely small damage and deformation in the sample susceptible to electron beam irradiation; and scarce adsorption gas.

Embodiment 1

Figure 1B:
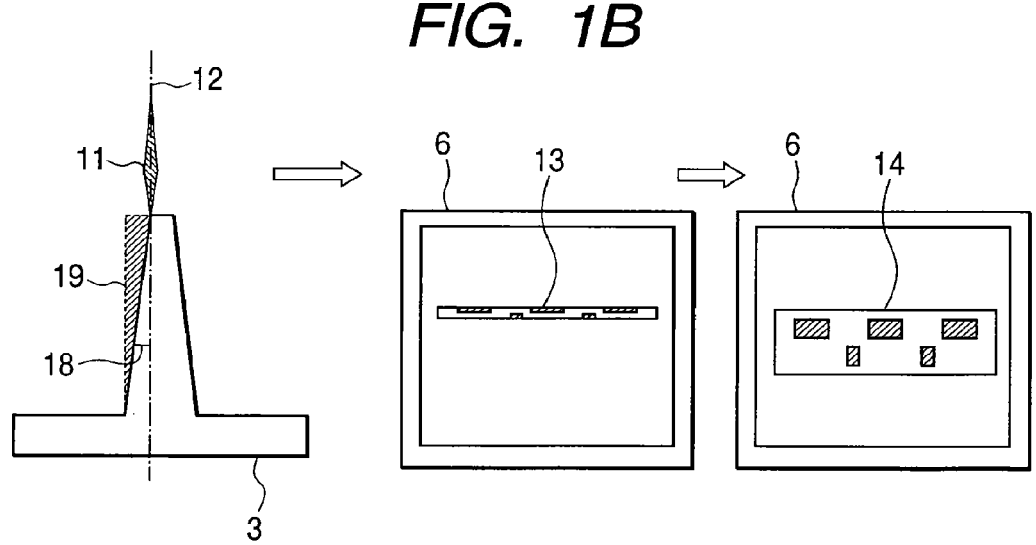

FIG. 1A is a general configuration diagram of a charged particle beam apparatus and FIG. 1B is a general configuration diagram on the display of a secondary particle image formed by ion beams during processing. In the present embodiment, the charged particle beam apparatus shown in FIGS. 1A and 1B comprises: an ion beam system 1 to generate and focus ion beams 11 and scan a sample 3 with the ion beams 11; a secondary particle detector 5 to detect secondary particles generated from the sample 3; a sample stage 4 on which the sample 3 is placed; a vacuum chamber 8 in which the sample stage 4 is placed; a display device 6 to display a secondary particle image 15 formed by the secondary particles; and a control device 7 to control constituent components. The control device 7 has the function of carrying out the following processes:
(1) A processed cross section by the ion beams 11 from the beam irradiation direction 12 incoming perpendicularly to the sample surface, in consideration of the relationship between a local angle of the ion beams incoming to a sample and a sputtering efficiency, has an angle 18 of about 3 to 6 degrees from the beam irradiation direction 12 to form cross section in nearly parallel with the beam irradiation direction 12. The control device 7 forms two cross sections (A) 9 and (B) 10 in nearly parallel with the beam irradiation direction 12 using the above process;
(2) A processed cross section by the ion beams 11 from the beam irradiation direction 12 incoming perpendicularly to the sample surface has an angle 18 of about 3 to 6 degrees. The inclined processed cross section provides a strip-shaped image observed from the beam irradiation direction 12, and the processed cross section in the region of the scanning area 19 can be observed as an processed strip-shaped secondary particle image. The control device 7 set a strip-shaped fabrication area 13 from the beam irradiation direction 12 using the above process; and
(3) The control device 7 displays the secondary particle image 15 during processing at least so as to expand the strip shape at least in the direction of the short side.

On the display device 6, as shown in FIG. 1B, a secondary particle image 13 is expanded in the process (3) and displayed as an image 14. At least two cross sections (A) 9 and (B) 10 or more are formed in the sample 3 and the processes (1), (2), and (3) are used at least once or more for the observation of the cross sections (A) 9 and (B) 10.

Since a cross section formed by FIB processing has an angle 18 of about 3 to 6 degrees from the beam irradiation direction 12, the cross section in the scanning area 19 of the ion beams can be observed as a secondary particle image 15 during processing even by the ion beams 11 incoming perpendicularly to the sample surface. The outline of a cross-sectional structure is obtained by displaying the strip-shaped secondary particle image in an expanded manner and it is possible to judge the cross-sectional structure by the ion beams incoming perpendicularly to the sample surface without a stage inclined. By so doing, it is possible to reduce or omit: the operation of interrupting processing in order to observe a cross section, switching the ion beams 11 from the ion beams for processing to ion beams for observation, and displacing (in X, Y, and Z directions, rotation, inclination, etc.) a sample stage 4 to a location where the cross section can be observed; the operation of interrupting processing and displacing the sample 3 to another apparatus such as an SEM or an STEM; or both the operations. Further, in the present invention, since the cross-sectional structure is observed at the same time with processing, switching from processing to observation is unnecessary. By those effects, it is possible to considerably improve the operation efficiency of processing and observation requiring accurate judgment of processing end in order to surely retain an intended defective portion while the defective portion is searched particularly in a sample the accurate defective portion of which is unknown. Although the case of processing and observing two cross sections is shown in the present embodiment, the number of the cross sections is not particularly limited and the orientations of the cross sections can be set arbitrarily. Further, a cross section is not necessarily planar but may be round. In a conventional case, since processing and observation are carried out alternately, the observation data of a cross section come to be discrete data such as images or the like. In the present embodiment, since processing and observation are carried out simultaneously, it is possible to obtain the observation data of a cross section not only as discrete data such as images but also as continuous data such as motion picture data.

Figure 3A:
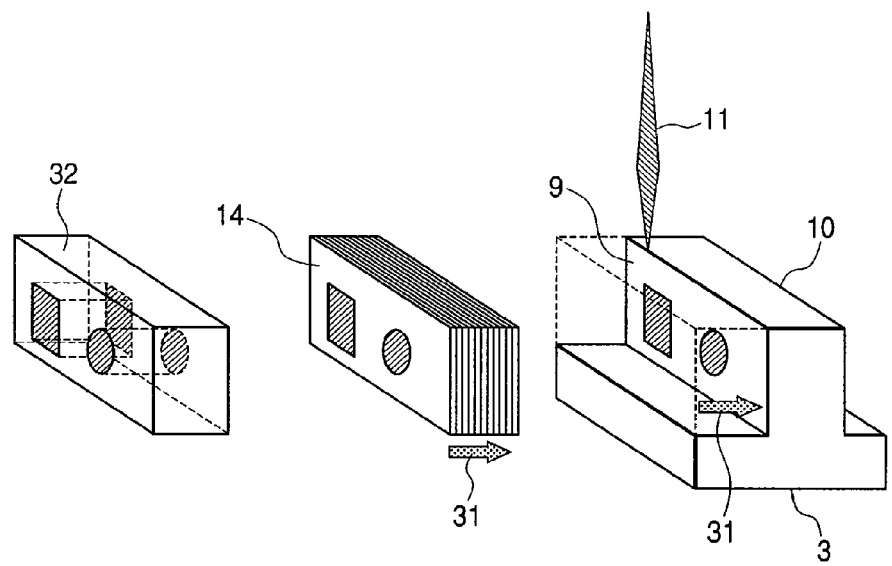
FIGS. 3A and 3B show an embodiment of three-dimensional data construction.
Figure 3B:
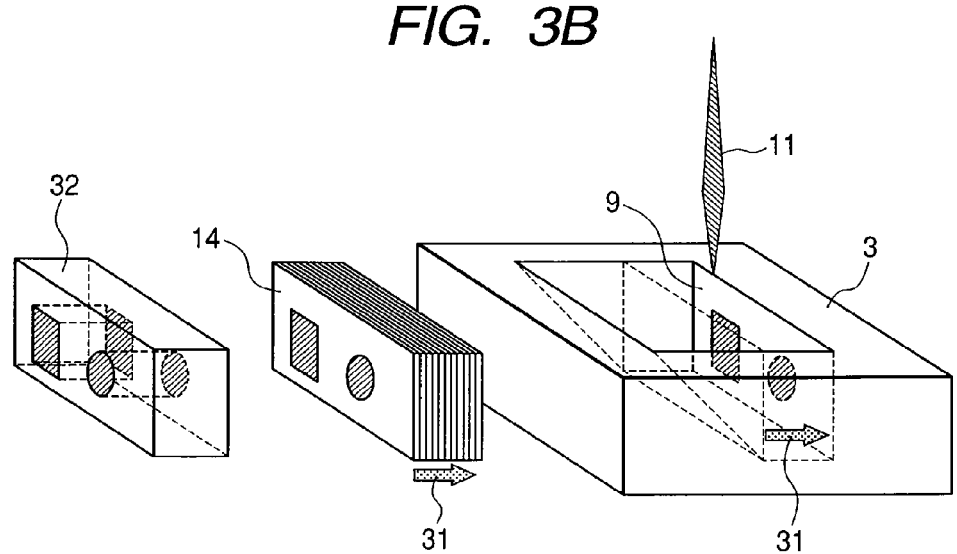

FIGS. 3A and 3B show an embodiment of three-dimensional data construction of the sample 3 according to the present embodiment 1. FIG. 3A shows an embodiment of three-dimensional data construction in a fabrication area of thin film processing and FIG. 3B shows an embodiment of three-dimensional data construction in a fabrication area of a bulk sample. The present embodiment shows three-dimensional data construction using discrete image data. Processing and observation are carried out continuously or intermittently and secondary particle images 14 expansively showing the cross section (A) 9 are obtained one by one and stored in relation to the positional information of the cross sections. The plural pieces of stored image data are aligned in the processing direction 31 of the cross sections, the linkage between adjacent images is complemented, and thereby the three-dimensional data (A) 32 of the sample 3 is constructed. Although the three-dimensional data is constructed in one fabrication area in the present embodiment, the number of the fabrication area may be plural. Further, not only images but also mapping data for elemental analysis may be accepted. It is also possible to construct seamless three-dimensional data (A) 32 of the sample 3 by using motion picture data. The constructed three-dimensional data (A) 32 may be corrected so that the dimensional ratio of length to width may conform to actual dimensional ratio of the sample 3.

Figure 4:
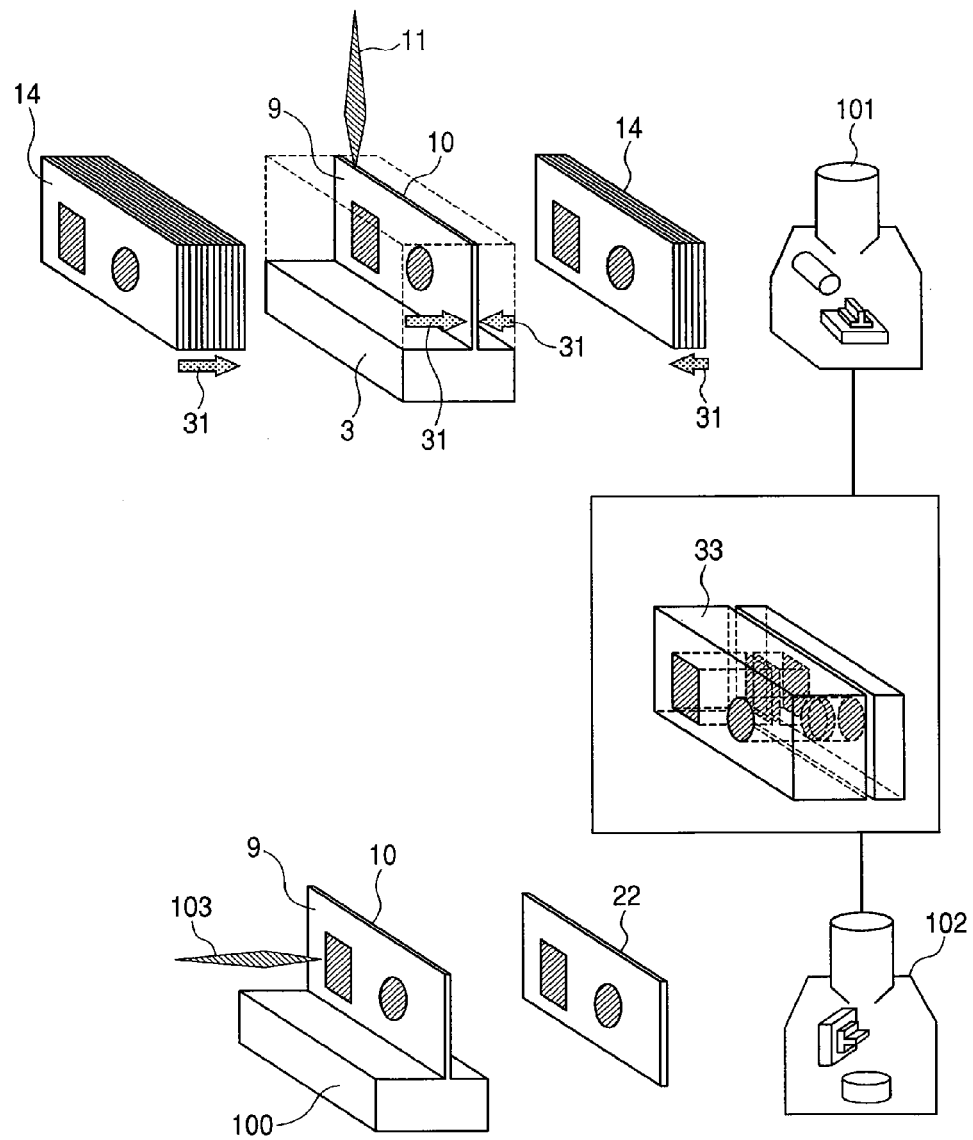
FIG. 4 shows an embodiment of three-dimensional data construction.

FIG. 4 shows another embodiment of three-dimensional data construction of the sample 3 in the embodiment 1. Processing and observation are carried out continuously or intermittently with a charged particle beam apparatus 101 according to the present invention and secondary particle images 14 expansively showing the cross section (A) 9 and the cross section (B) 10 are obtained one by one and stored in relation to the positional information of the cross sections. The sample 3 is subjected to thin film processing until a film thickness through which electron beams 103 pass is obtained. Successively, the processed sample 100 is transferred to another electron beam apparatus 102 and a transmitted particle image 22 of the processed sample 100 is obtained. The data is also stored in relation to the positional information in the sample 3.

The plural pieces of image data obtained and stored with the charged particle beam apparatus 101 are corrected so that the dimensional ratio of length to width may conform to the actual dimensional ratio of the sample 3 and aligned in the processing direction 31 of the cross sections. Then image data obtained and stored with another electron beam apparatus 102 is added to the data group, the linkage between adjacent images is complemented, and thereby the three-dimensional data (B) 33 of the sample 3 are constructed. In the case of the present embodiment, the data is produced by synthesizing a scanning ion microscopic image (an SIM image) formed by ion beams 11 and a transmission electron microscopic image (a TEM image). The data obtained with another electron beam apparatus 102 may be a secondary electron image or a reflected electron (backscattered electron) image. The data obtained with the charged particle beam apparatus 101 may be motion picture data.

Embodiment 2

Figure 2A:
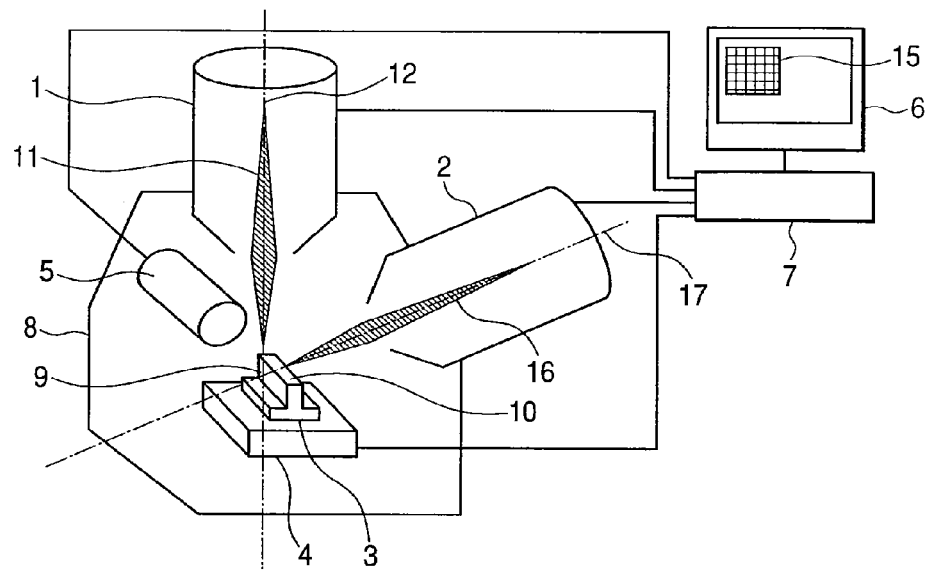
FIGS. 2A and 2B are general configuration diagrams of a charged particle beam apparatus having an ion beam system and an electron beam system.
Figure 2B:
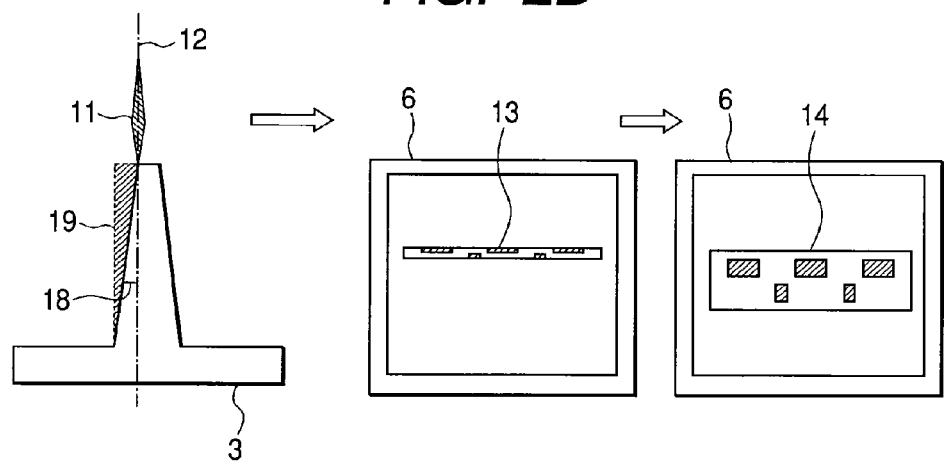

FIGS. 2A and 2B show an embodiment of a charged particle beam apparatus having an ion beam system and an electron beam system. FIG. 2A is a general configuration diagram of a charged particle beam apparatus and FIG. 2B is, same as FIG. 1B, a general view explaining the display of a secondary particle image formed by ion beams during processing. The present embodiment is a composite device formed by adding an electron beam system 2 to generate electron beams 16, focus them, and scan a sample with them to the embodiment shown in FIGS. 1A and 1B. The ion beam system 1 and the electron beam system 2 are disposed so that the beam irradiation direction 12 of the ion beams 11 may intersect with the electron beam irradiation direction 17 of the electron beams 16 at a certain point. A sample 3 is placed in the vicinity of the point where the beam irradiation direction 12 of the ion beams 11 intersects with the electron beam irradiation direction 17 of the electron beams 16. Either of the cross section (A) 9 or the cross section (B) 10, the cross section (B) 10 in the present embodiment, is formed at the position that can be irradiated with the electron beams 16. In the present embodiment, in addition to the effects in the embodiment 1 shown in FIGS. 1A and 1B, it is possible to: observe the cross section (B) 10 at a high resolution by using the electron beam system 2; and obtain a more detailed cross-sectional structure. When high resolution observation with the electron beam system 2 is used for judging the end of processing, it is possible to judge the end of processing with a higher degree of accuracy.

Figure 5:
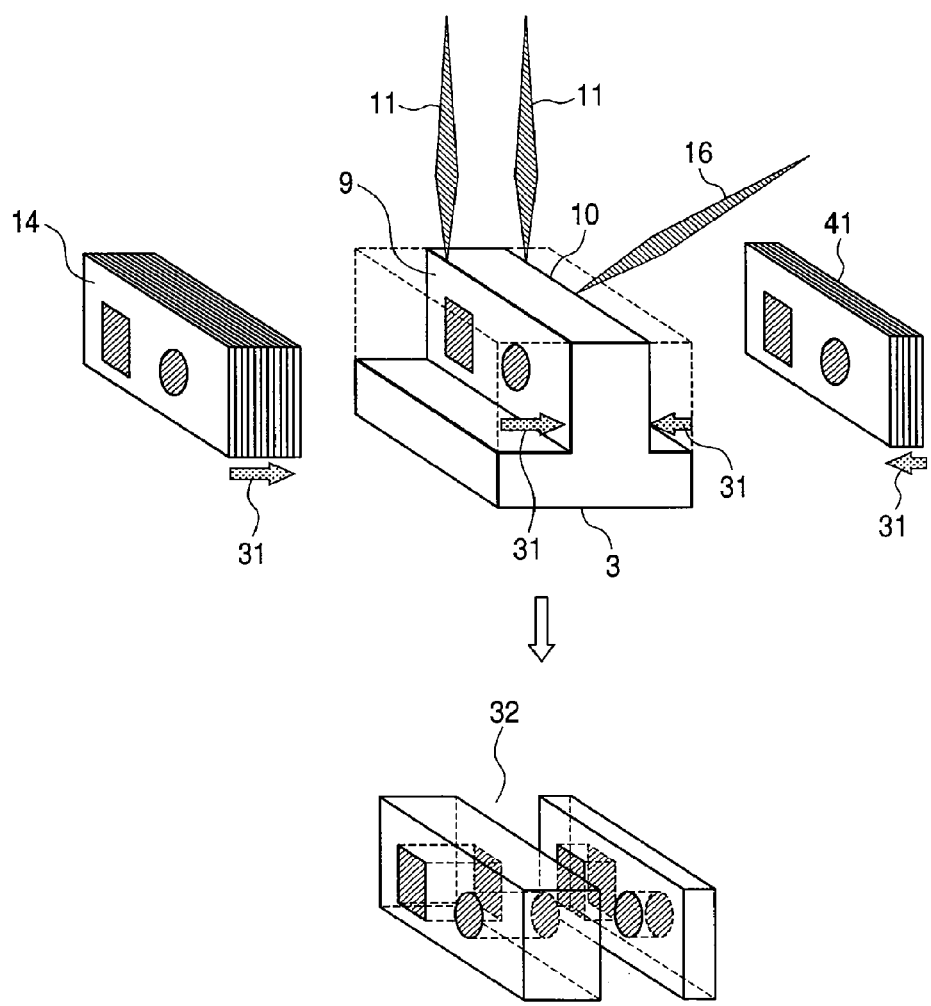
FIG. 5 shows an embodiment of three-dimensional data construction.
Figure 7:
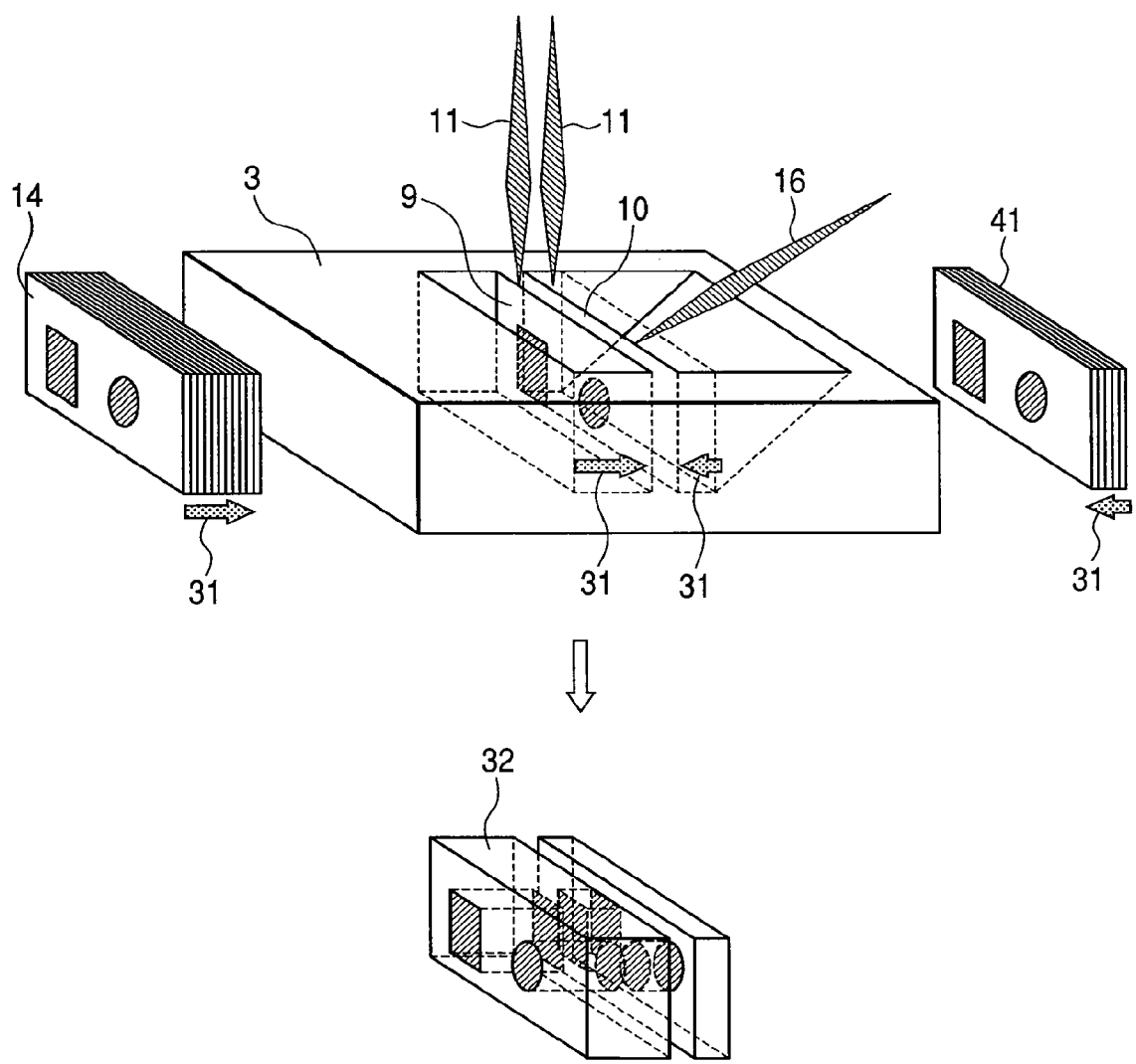
FIG. 7 shows an embodiment of three-dimensional data construction.

FIG. 5 shows an embodiment of three-dimensional data construction of the sample 3 used in the embodiment 2 shown in FIGS. 2A and 2B. The present embodiment shows three-dimensional data construction formed by using discrete image data. Processing and observation are carried out continuously or intermittently and secondary particle images 14 expansively showing the cross section (A) 9 are obtained one by one and stored in relation to the positional information of the cross sections. In the case of the cross section (B) 10, secondary particle images 41 are obtained one by one by electron beams 16 and stored in relation to the positional information of the cross sections. The stored plural pieces of image data are corrected so that the dimensional ratio of length to width may conform to the actual dimensional ratio of the sample 3 and aligned in the processing direction 31 of the cross sections, the linkage between adjacent images is complemented, and thereby the three-dimensional data (A) 32 of the sample 3 is constructed. Although the three-dimensional data is constructed in two fabrication areas in the present embodiment, the number of the fabrication areas may be two or more. Further, not only images but also mapping data for elemental analysis may be accepted. In the case of the cross section (A) 9, it is also possible to construct seamless three-dimensional data of the sample 3 by using motion picture data. In the case of the cross section (B) 10, the data obtained by electron beams 16 and the data obtained by ion beams 11 may be mixed to form mixed data. Although the explanations are made on the basis of the case of processing a sample into a convex shape in the present embodiment, it is also possible to construct three-dimensional data (A) 32 by forming a thin film portion in a bulk sample as shown in FIG. 7.

Embodiment 3

Figure 6A:
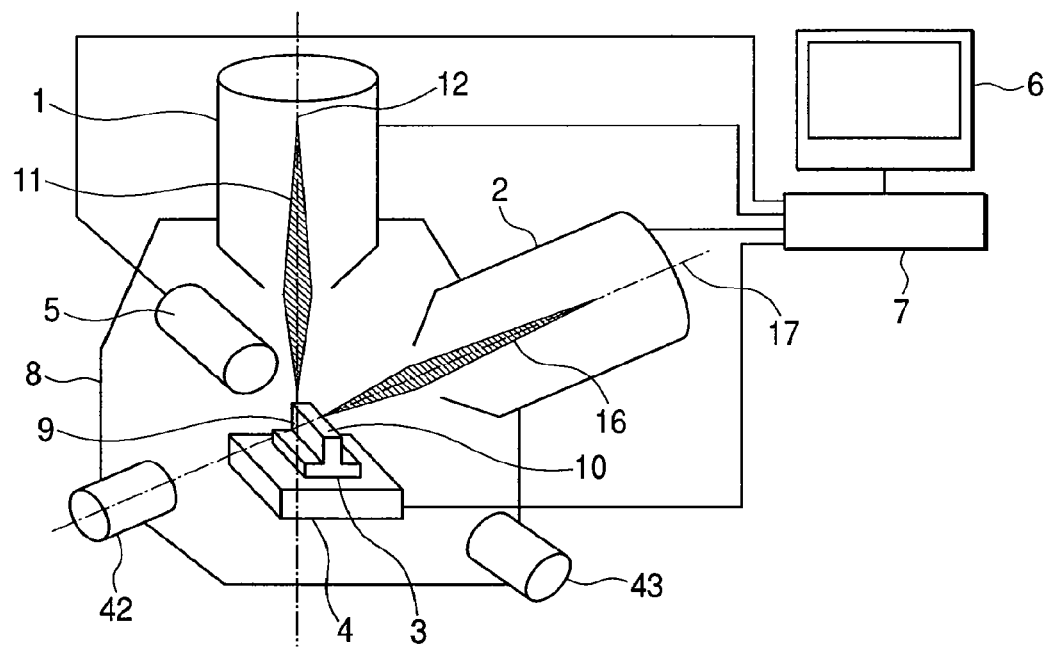
FIGS. 6A and 6B show a general configuration diagram of a charged particle beam apparatus having an ion beam system and an electron beam system and an embodiment of three-dimensional data construction.
Figure 6B:
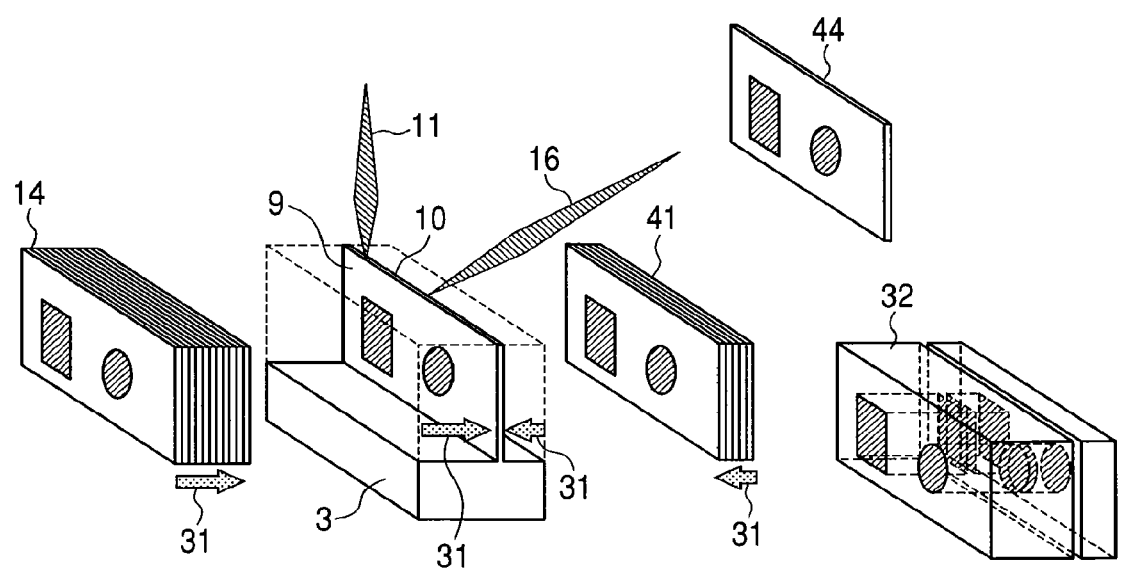

FIGS. 6A and 6B show another embodiment of a charged particle beam apparatus having an ion beam system and an electron beam system. FIG. 6A is a general configuration diagram of a charged particle beam apparatus and FIG. 6B is a general view explaining the three-dimensional data construction of the sample 3. The present embodiment is a composite device formed by adding a transmission electron detector 42 to detect transmitted electrons and a reflected electron detector 43 to detect reflected electrons (backscattered electrons) to the embodiment 2 shown in FIGS. 2A and 2B. In the observation of thin film cross sections of the sample 3, the cross section (B) 10 facing electron beams 16 is observed by a secondary electron image 41 formed by electron beams and the end of processing is judged and the cross section (A) 9 is observed by an expansively displayed secondary electron image 14 and the end of the processing is judged. Then the thin film is processed to an intended region without the movement of a stage. A transmission electron image 44 is obtained from the produced thin film sample with the transmission electron detector 42 and observed at a high resolution. It is possible to obtain a reflected electron (backscattered electron) image by detecting not only transmitted electrons but reflected electrons (backscattered electrons). Further, it is possible to construct three-dimensional data (A) 32 similar to that of the embodiment shown in FIG. 5. The aforementioned processing and observation can be carried out in a charged particle beam apparatus and hence the sample 3 is never exposed to the air and it is possible to observe or analyze a clean surface having no adsorbed gas. By installing a heater in the vacuum chamber 8, it is possible to further reduce the gas adsorbed on the surface and observe and analyze a cleaner surface.

Figure 8:
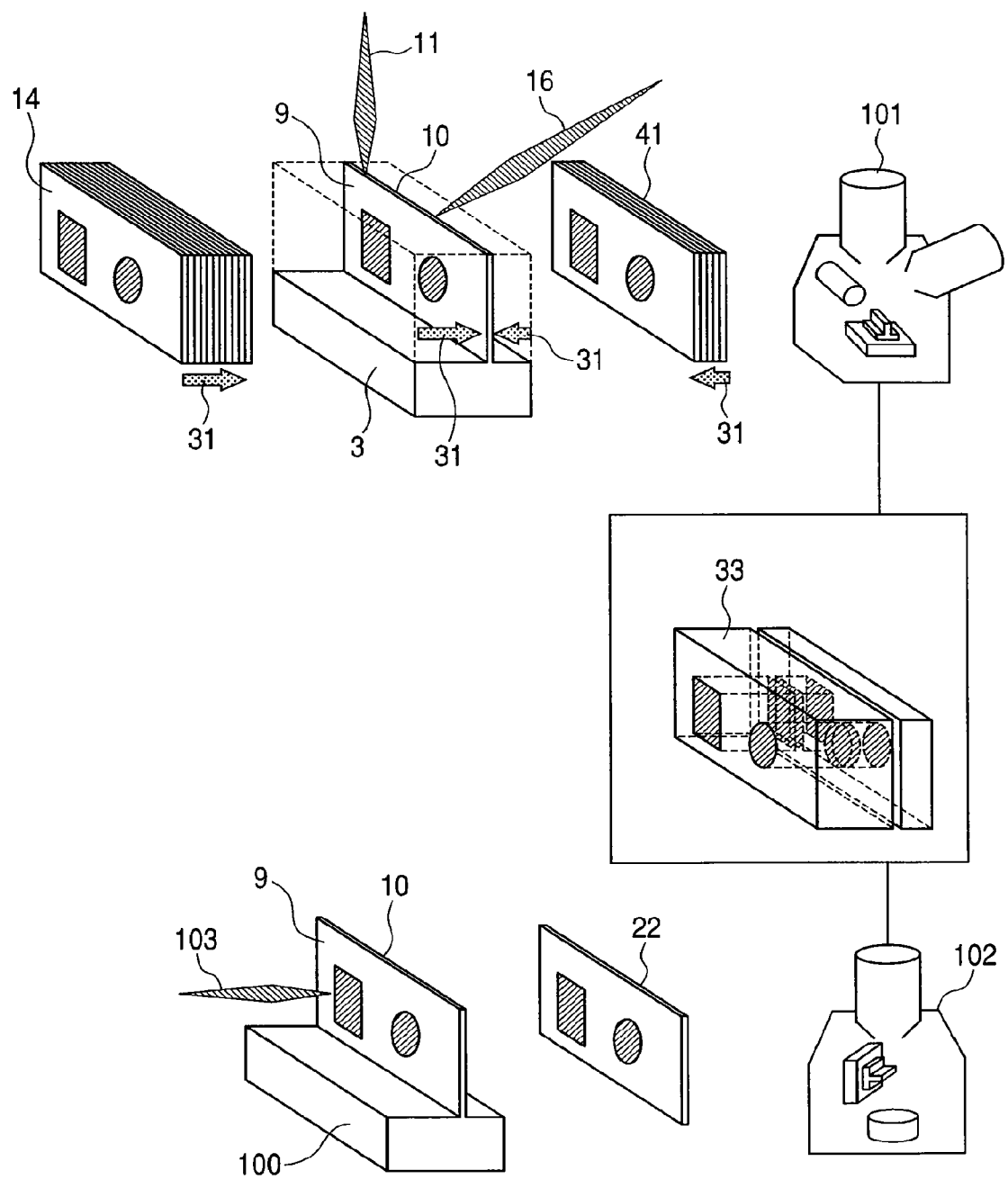
FIG. 8 shows an embodiment of three-dimensional data construction.

FIG. 8 shows an embodiment wherein the three-dimensional data described in FIG. 4 is constructed with a charged particle beam apparatus having an ion beam system 1 and an electron beam system 2 shown in FIGS. 2A and 2B or 6. With the charged particle beam apparatus 101 according to the present invention too, a sample can be observed at a high resolution by electron beams 16. In the charged particle beam apparatus 101, a sample is observed at an acceleration voltage of 30 kV with an STEM, successively the processed sample 100 is transferred to another electron beam apparatus 102, and the sample is observed at a higher resolution at an acceleration voltage of 200 kV with the STEM. The three-dimensional data (B) 33 is constructed with the data.

[Display Device]

Figure 9:
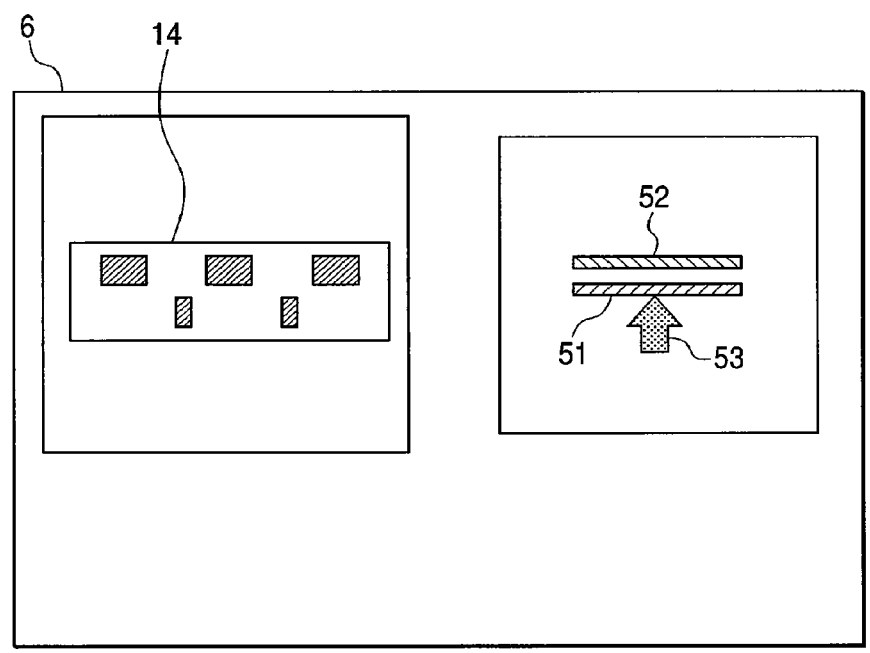
FIG. 9 shows an embodiment of cross-sectional image display.

FIG. 9 is an embodiment showing how to specify the cross sectional image of the sample 3 corresponding to the secondary particle image 14 expansively displayed on the display device 6. On the display device 6, the secondary particle image 14 is expansively displayed together with the set processing pattern (A) 51 and processing pattern (B) 52. An operator is informed of which processing pattern is processed and observed as the expansively displayed secondary particle image 14 by indicating the corresponding processing pattern with the arrow 53.

Figure 10A:
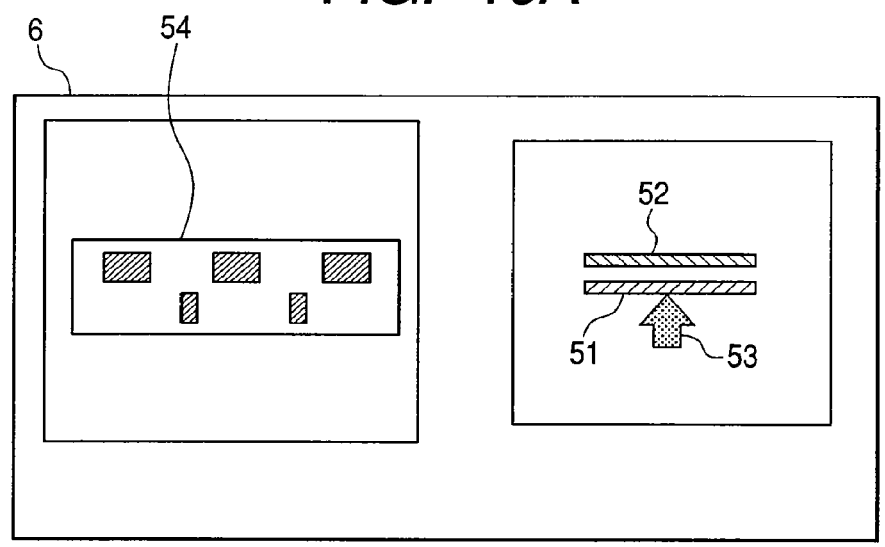
FIGS. 10A and 10B show an embodiment of cross-sectional image display.
Figure 10B:
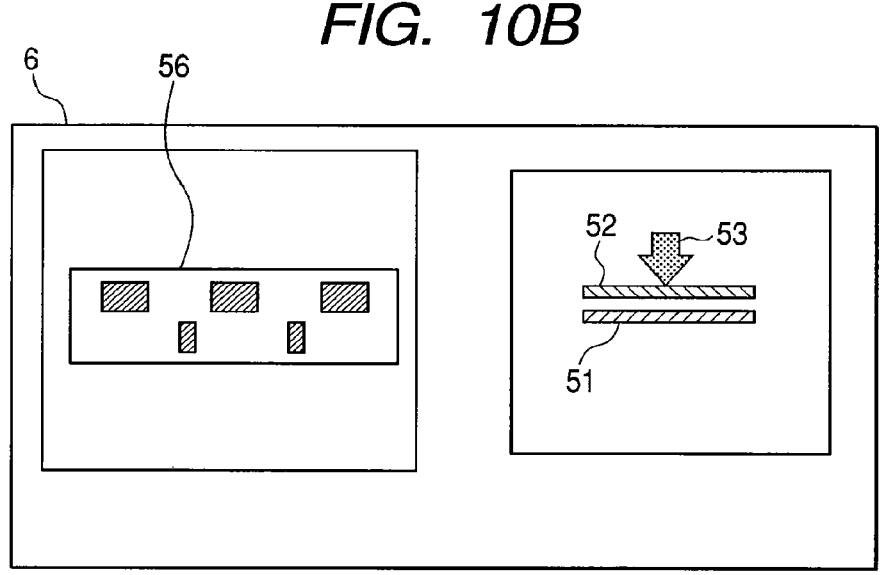
Figure 11A:
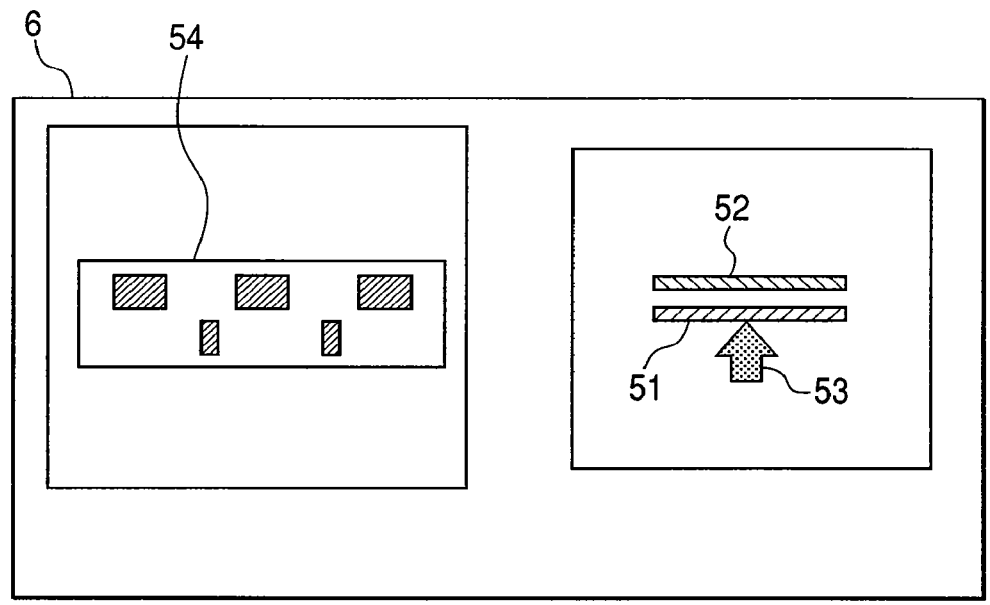
FIGS. 11A and 11B show an embodiment of cross-sectional image display.
Figure 11B:
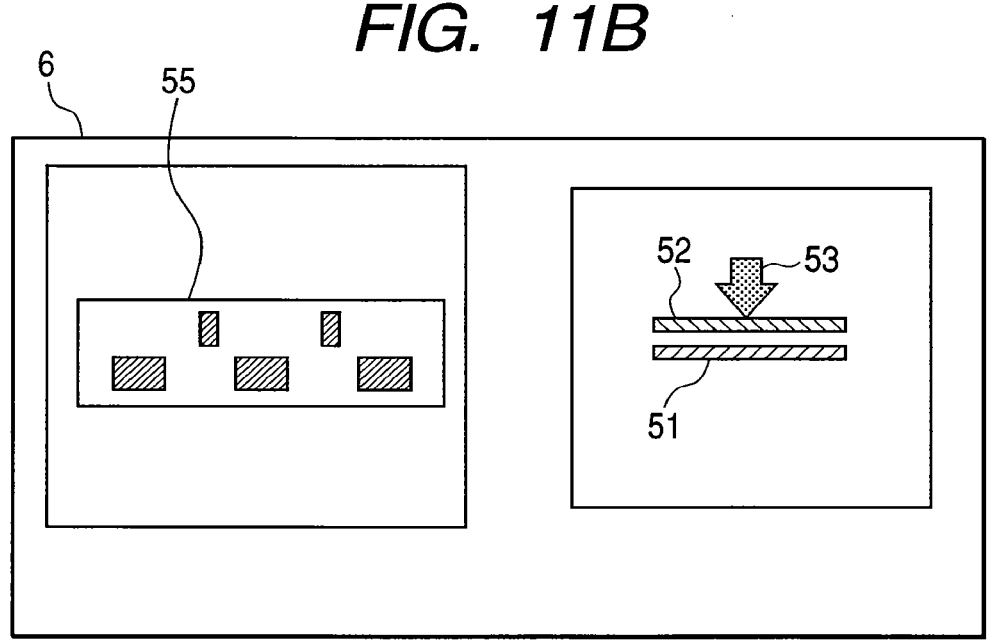

FIGS. 10 and 11 are other embodiments showing which cross-sectional image of the sample 3 corresponds to the secondary particle image 14 expansively displayed on the display device 6. In the embodiment of FIGS. 10A and 10B, the corresponding processing pattern is indicated with the arrow 53 and the display manner of the secondary particle image expansively displayed is changed for each set processing pattern. In the embodiment, an operator is informed of the cross-sectional image now processed and observed by displaying the expansively displayed secondary particle image (A) 54 and the expansively displayed secondary particle image (C) 56 inversely in the vertical direction. Meanwhile, the embodiment shown in FIGS. 11A and 11B is the opposite of that shown in FIGS. 10A and 10B. That is, all the expansively displayed cross-sectional images are displayed in the same direction so that an operator may judge the cross-sectional images. In the present embodiment, the expansively displayed secondary particle image (A) 54 and the expansively displayed secondary particle image (B) 55 are displayed in the same direction and an operator is informed of the currently processed and observed cross section by indicating the corresponding processing pattern with the arrow 53 in the same way as the embodiment shown in FIG. 9. Here, in the embodiment, the case of two cross sections is shown but the number of cross sections is not limited.

Figure 12:
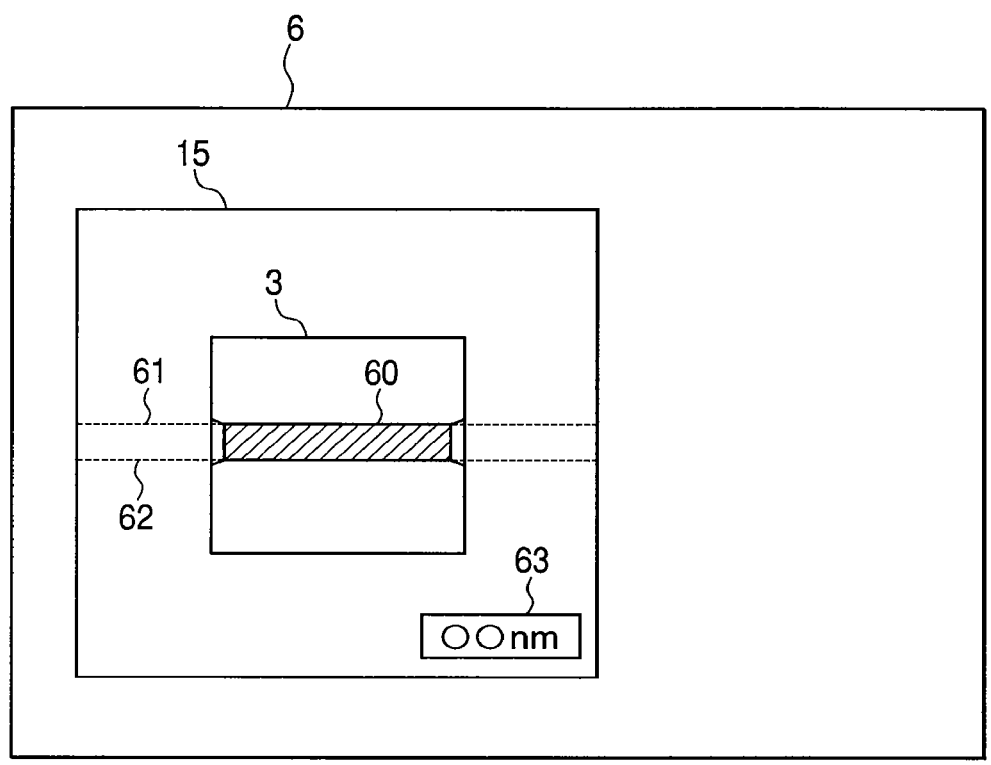
FIG. 12 shows an embodiment of thin film thickness measurement.

FIG. 12 shows an embodiment of monitoring and measuring the thickness of the thin film portion 60 in the sample 3. A secondary particle image 15 wherein the thickness of the thin film portion is observed is displayed on the display device 6, the thickness of the thin film portion 60 is automatically measured when two long side cursors of the thin film portion 60, a cursor (A) 61 and a cursor (B) 62, are adjusted and the measured value is displayed on the thickness display unit 63 in the display device 6. It is possible to judge the processing end more accurately by using the information on the thickness of the thin film portion 60 for the judgment of the processing end.

Figure 13:
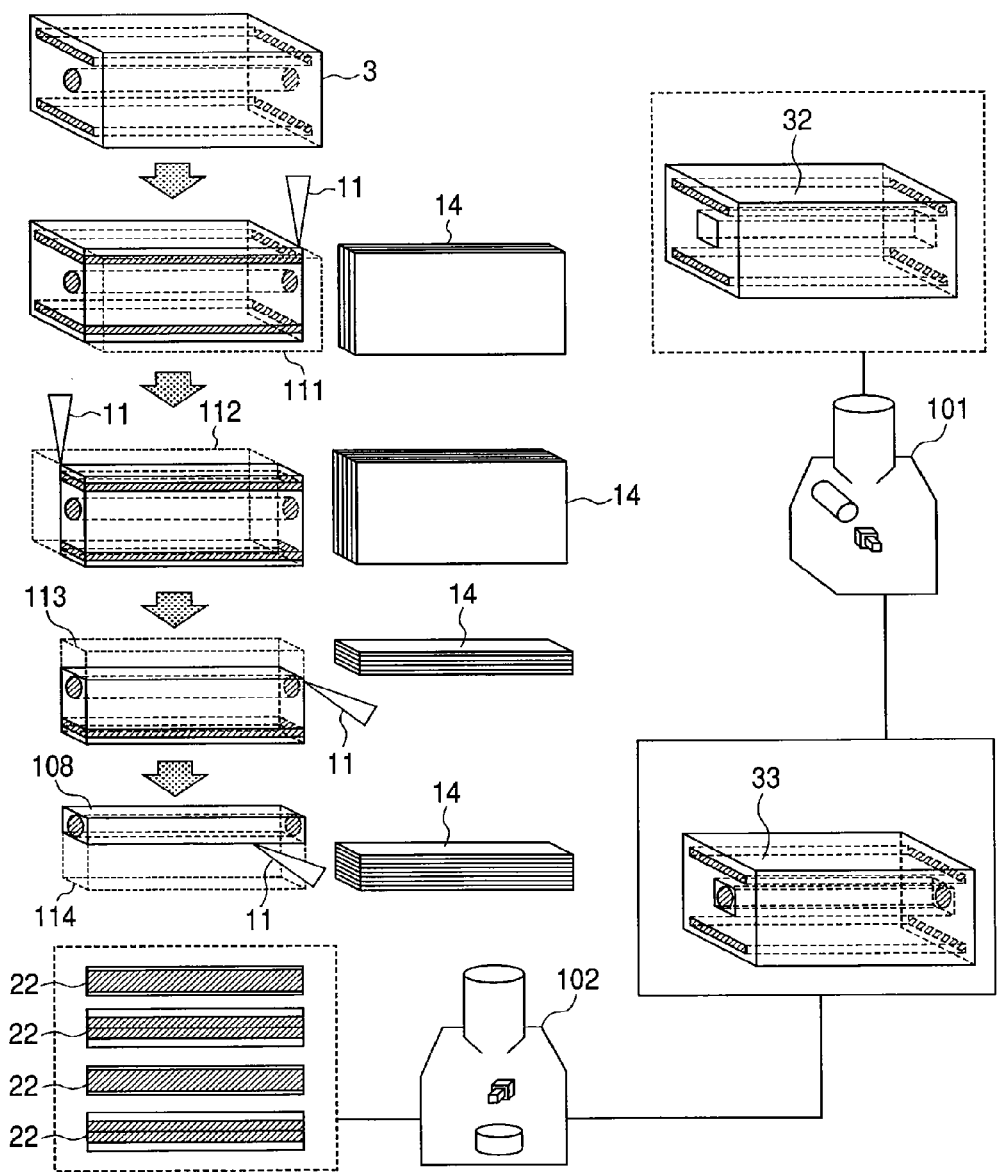
FIG. 13 shows an embodiment of three-dimensional data construction.

FIG. 13 shows an embodiment of constructing three-dimensional data of a prismatic micro-column with a charged particle beam apparatus 101 and another electron beam apparatus 102 according to the present invention. The structural analysis of a prismatic micro-column 108 has heretofore been done by: removing a fabrication area (A) 111, a fabrication area (B) 112, a fabrication area (C) 113, and a fabrication area (D) 114 from a bulk sample 3 by ion beams 11; forming the prismatic micro-column 108 as a fine columnar sample; thereafter transferring the prismatic micro-column 108 to an STEM or a TEM; and observing transmitted particle images 22 at a high resolution from various directions. On this occasion, in order to prevent throughput from lowering, information on the fabrication area (A) 111, the fabrication area (B) 112, the fabrication area (C) 113, and the fabrication area (D) 114 is rejected. That is, such an operation as to interrupt the processing and observe the cross sections during the processing of the fabrication area (A) 111, the fabrication area (B) 112, the fabrication area (C) 113, and the fabrication area (D) 114 is not carried out. In the present embodiment, since a cross section can be observed simultaneously during processing by the charged particle beam apparatus, it is possible to obtain the cross-sectional information of the fabrication area (A) 111, the fabrication area (B) 112, the fabrication area (C) 113, and the fabrication area (D) 114 while the throughput is not lowered. The cross-sectional information corresponding to the four fabrication areas is stored as the three-domentional data (A) 32, in relation to the positional information showing the locations of the cross sections in the sample 3 and the three-dimensional data (B) 33 of the sample 3 is constructed by combining the stored information with the information on the structure of the prismatic micro-column 108 observed with another electron beam apparatus 102, on this occasion an STEM or a TEM. The information used for the construction of the three-dimensional data (B) 33 is not necessarily a cross-sectional image of the same size as described in FIGS. 4 and 8.

Figure 14:
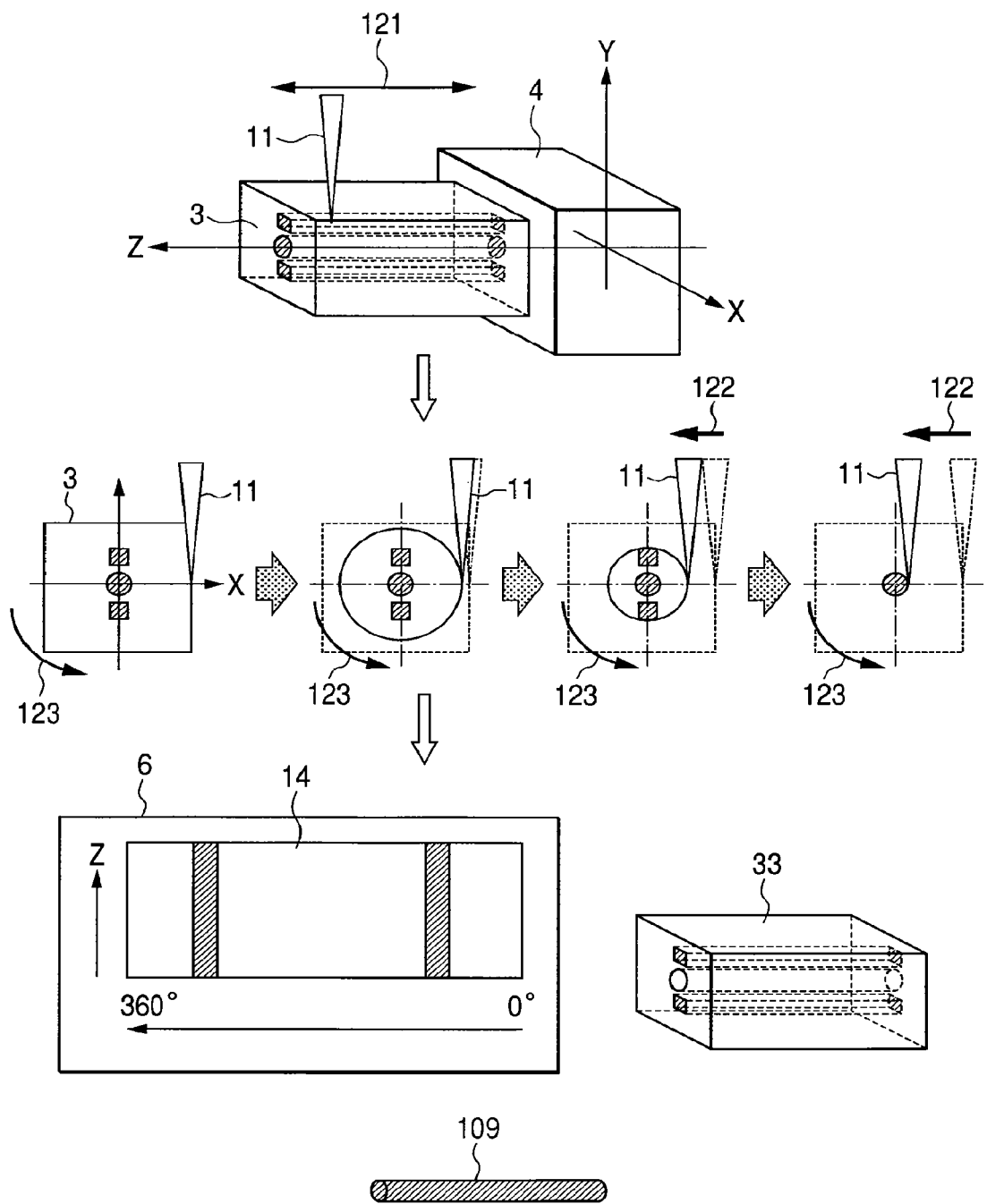
FIG. 14 shows an embodiment of three-dimensional data construction.

FIG. 14 shows an embodiment of the three-dimensional data construction of a micro-cylinder. A micro-cylinder 109 as a fine columnar sample is produced by: rotating a sample stage 4 in the sample rotation direction 123 while a sample is scanned with ion beams 11 in the scanning direction 121; and gradually moving the ion beams 11 toward the shift direction 122. In the present embodiment, the number of the cross-sectional image is one because the sample 3 is rotated and processed into a columnar shape. The display device 6 displays an expansively displayed secondary particle image 14 so as to be viewed panoramically from the rotation axis of the sample. It is possible to construct the three-dimensional data (B) 33 of the sample 3 by combining the data in the radius direction. It is also possible to construct such a three-dimensional data as described in FIG. 13 by transferring a microcolumn 109 to another electron beam apparatus and subjecting it to structural analysis.

Figure 15:
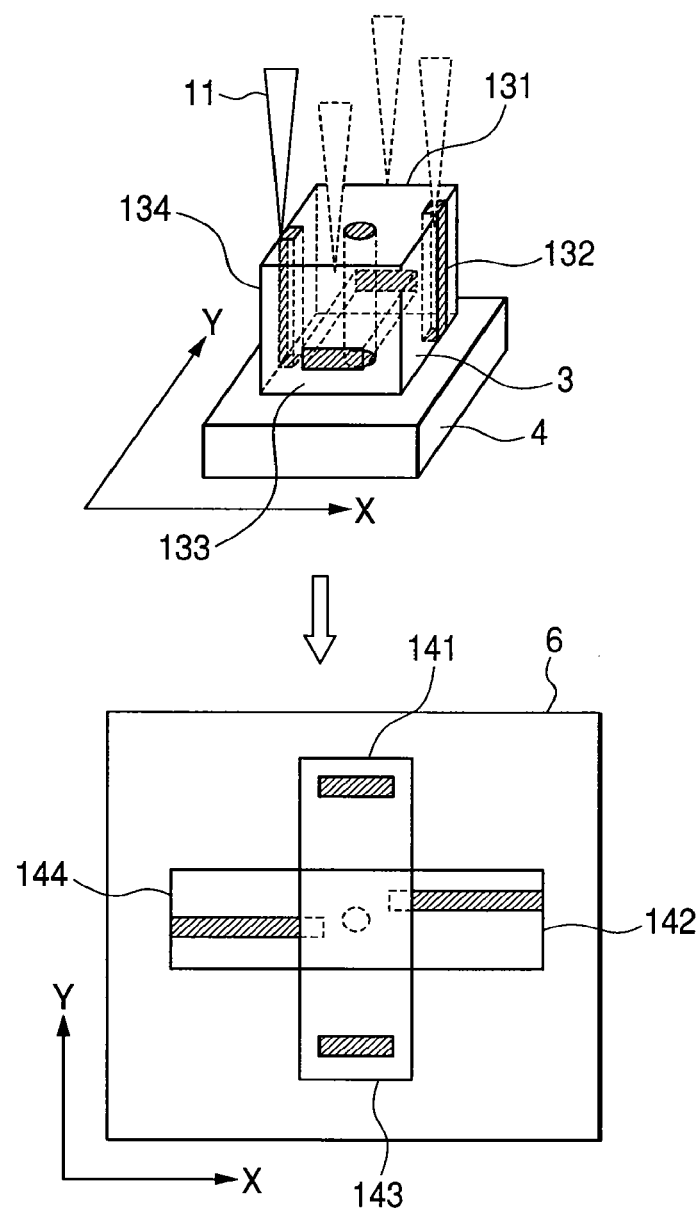
FIG. 15 shows an embodiment of cross-sectional image display.

FIG. 15 shows an embodiment of displaying an expansively displayed secondary particle image when four cross sections are processed and observed. The sample 3 is irradiated from above with ion beams 11 and the four cross sections (C) 131, (D) 132, (E) 133, and (F) 134 are processed and observed. The upper surface image and the cross-sectional images (C) 141, (D) 142, (E) 143, and (F) 144 on the four sides of the sample 3 are displayed on the display device 6 like a development view in place of displaying each cross-sectional image individually on the display device 6 as shown in FIGS. 9, 10, and 11. The processing end is judged while the upper surface image and the four cross-sectional images of the sample 3 are observed.

In the present embodiments, it is possible to produce an accurate sample with a high throughput without an intended region lost in the process for producing a sample such as a thin film while processing and monitoring of a processed cross section are repeated even with a sample the accurate defective position of which is not known. Further, it is possible to improve analysis throughput in a process of repeating processing and monitoring of a processed cross section and analyzing the three-dimensional structure of the sample. Furthermore, it is possible to observe a cross section extremely close to the true feature even with a material very susceptible to electron beam irradiation.

What is claimed is:

1. A charged particle beam apparatus, comprising:
   a sample stage on which a sample is placed;
   a vacuum chamber to contain said sample stage;
   an ion beam system to generate and focus ion beams and scan said sample with said ion beams;
   a secondary particle detector to detect secondary particles generated from said sample;
   a display device to display a secondary particle image formed by said secondary particles;
   wherein said charged particle beam apparatus:
   processes at least two cross sections in the sample by the ion beams, and shifts the processed cross sections to the direction perpendicular to the cross sections and repeats the processing to produce a thin film sample, and
   wherein said charged particle beam apparatus sets strip-shaped ion beam fabrication areas in the region containing said cross section from the direction of said ion beams in a cross section nearly parallel with the direction of said ion beams;
   processes said fabrication area by said ion beams;
   displays two of said strip-shaped ion beam fabrication areas and a secondary particle image of said strip-shaped ion beam fabrication area being processed by the ion beam in the display device;
   displays expansively in a asymmetrical way the secondary particle image of the strip-shaped fabrication area processed by the ion beam at least in a short side of the strip-shaped image to judge the cross-sectional structure of the sample, and
   indicates which strip-shaped ion beam fabrication area is under processing; and
   obtains the plural secondary particle images expanded at least in a short side of the strip-shaped image as a motion picture data.

2. The charged particle beam apparatus according to claim 1, wherein said secondary particle image expanded at least in the direction of the short side of the strip-shaped area is used for judging the end of the processing by said ion beams.

* * * * *